(12) United States Patent
Franklin et al.

(10) Patent No.: US 10,918,121 B2
(45) Date of Patent: *Feb. 16, 2021

(54) METHOD FOR CONDUCING CONCENTRATED CANNABIS OIL TO BE STABLE, EMULSIFIABLE AND FLAVORLESS FOR USE IN HOT BEVERAGES AND RESULTING POWDERIZED CANNABIS OIL

(71) Applicant: BETTERLIFE PHARMA US INC., Seattle, WA (US)

(72) Inventors: Ross M. Franklin, Farmers Branch, TX (US); Ed Rosenthal, Oakland, CA (US); Rachel M. Franklin, Farmers Branch, TX (US)

(73) Assignee: BETTERLIFE PHARMA US INC., Seattle, WA (US)

( * ) Notice: Subject to any disclaimer, the term of this patent is extended or adjusted under 35 U.S.C. 154(b) by 260 days.

This patent is subject to a terminal disclaimer.

(21) Appl. No.: 16/203,547

(22) Filed: Nov. 28, 2018

(65) Prior Publication Data
US 2019/0090515 A1 Mar. 28, 2019

Related U.S. Application Data

(63) Continuation of application No. 15/466,068, filed on Mar. 22, 2017, now Pat. No. 10,165,790, which is a
(Continued)

(51) Int. Cl.
| | |
|---|---|
| *A61K 36/00* | (2006.01) |
| *A23L 2/395* | (2006.01) |
| *A61K 36/185* | (2006.01) |
| *A61K 31/352* | (2006.01) |
| *A61K 9/14* | (2006.01) |
| *A61K 9/00* | (2006.01) |
| *A23F 3/40* | (2006.01) |
| *A23L 2/56* | (2006.01) |
| *A23L 2/52* | (2006.01) |
| *A23L 29/30* | (2016.01) |
| *A23L 27/10* | (2016.01) |
| *A23D 9/007* | (2006.01) |
| *A23D 9/05* | (2006.01) |
| *A23D 9/02* | (2006.01) |
| *A23F 5/00* | (2006.01) |
| *A23L 33/105* | (2016.01) |
| *A21D 13/44* | (2017.01) |
| *A21D 13/80* | (2017.01) |
| *B65D 85/804* | (2006.01) |
| *B65D 85/808* | (2006.01) |
| *G01N 33/94* | (2006.01) |
| *A23L 7/143* | (2016.01) |
| *A61K 9/20* | (2006.01) |
| *A61K 9/48* | (2006.01) |
| *A61K 38/02* | (2006.01) |

(Continued)

(52) U.S. Cl.
CPC .............. *A23L 2/395* (2013.01); *A21D 13/44* (2017.01); *A21D 13/80* (2017.01); *A23D 9/007* (2013.01); *A23D 9/02* (2013.01); *A23D 9/05* (2013.01); *A23F 3/405* (2013.01); *A23F 5/00* (2013.01); *A23L 2/52* (2013.01); *A23L 2/56* (2013.01); *A23L 7/143* (2016.08); *A23L 27/10* (2016.08); *A23L 29/35* (2016.08); *A23L 33/105* (2016.08); *A61K 9/0056* (2013.01); *A61K 9/0095* (2013.01); *A61K 9/146* (2013.01); *A61K 9/20* (2013.01); *A61K 9/48* (2013.01); *A61K 31/352* (2013.01); *A61K 36/185* (2013.01); *A61K 38/02* (2013.01); *A61K 47/36* (2013.01); *A61K 47/38* (2013.01); *A61K 47/44* (2013.01); *B65D 85/808* (2013.01); *B65D 85/8046* (2013.01); *G01N 33/948* (2013.01); *A23V 2002/00* (2013.01); *A61K 2236/37* (2013.01); *Y02W 90/10* (2015.05)

(58) Field of Classification Search
CPC ...................................................... A61K 36/00
USPC ........................................................ 424/725
See application file for complete search history.

(56) References Cited

U.S. PATENT DOCUMENTS

| 5,127,953 A | 7/1992 | Hamaguchi |
| 2004/0033280 A1 | 2/2004 | Whittle |

(Continued)

FOREIGN PATENT DOCUMENTS

| EP | 0289063 A2 | 11/1988 |
| KR | 1020050021003 A | 4/2005 |

(Continued)

OTHER PUBLICATIONS

Bowles EJ. The Chemistry of Aromatherapeutic Oils. 3rd edn. Crow's Nest, NSW: Allen & Unwin; 2003 https://www.amazon.com/Chemistry-Aromatherapeutic-Oils-Joy-Bowles/dp/174114051X.

(Continued)

*Primary Examiner* — Michael V Meller
(74) *Attorney, Agent, or Firm* — Shumaker, Loop & Kendrick, LLP

(57) ABSTRACT

A method for producing powderized cannabis oil, and the resulting powderized cannabis oil, in which concentrated cannabis oil is mixed with and absorbed by a modified starch powder, preferably maltodextrin, in a ratio of at least three grams of starch powder for every one-eighth of a gram of cannabis oil is disclosed. Further disclosed are beverages, baked goods and single-serve beverage brewing cartridges utilizing or incorporating the powderized cannabis oil to (Continued)

create human-consumable products that contain an emulsified, tasteless, and odorless dose of cannabis oil.

13 Claims, 6 Drawing Sheets

Related U.S. Application Data continuation of application No. 15/049,916, filed on Feb. 22, 2016, now Pat. No. 9,629,886.

(60) Provisional application No. 62/120,275, filed on Feb. 24, 2015.

(51) Int. Cl.
*A61K 47/36* (2006.01)
*A61K 47/38* (2006.01)
*A61K 47/44* (2017.01)

(56) References Cited

U.S. PATENT DOCUMENTS

2008/0175902 A1 7/2008 Zajicek
2013/0274321 A1 10/2013 Newland

FOREIGN PATENT DOCUMENTS

WO 2013009928 A1 1/2013
WO 2013138906 A1 9/2013

OTHER PUBLICATIONS

Buchbauer G. Biological activities of essential oils. In: Baser KHC, Buchbauer G, editors. Handbook of Essential Oils:Science, Technology, and Applications. Boca Raton, FL: CRC Press; 2010. pp. 235-280. https://ttngmai.files.wordpress.com/2012/09/handbookofessentionaloil.pdf
Adams TB, Taylor SV. Safety evaluation of essential oils: a constituent-based approach. In: Baser KHC, Buchbauer G, editors. Handbook of Essential Oils: Science, Technology, and Applications. Boca Raton, FL: CRC Press; 2010. pp. 185-208 https://www.taylorfrancis.com/books/e/9781466590472/chapters/10.1201%2Fb19393-12.
Russo EB. The solution to the medicinal cannabis problem. In: Schatman ME, editor. Ethical Issues in Chronic Pain Management. Boca Raton, FL: Taylor & Francis; 2006. pp. 165-194 http://cannabisplus.net/cannabis-research-pdf/Pain/Russo%20Solution%20to%20the%20Medicinal%20Cannabis%20Problem%20%28in%20Schatman,%20Ethical%20Problems%20in%20Ethical%20Issues%20in%20Chronic%20Pain%20Management%29.pdf.
Review Human cannabinoid pharmacokinetics. Huestis MA Chem Biodivers. Aug. 2007; 4(8):1770-804. https://www.ncbi.nlm.nih.gov/pmc/articles/PMC2689518/.
Effects of citrus fragrance on immune function and depressive states. Komori T, Fujiwara R, Tanida M, Nomura J, Yokoyama MM Neuroimmunomodulation. May-Jun. 1995; 2(3):174-80. https://www.ncbi.nlm.nih.gov/pubmed/8646568.
d-limonene exposure to humans by inhalation: uptake, distribution, elimination, and effects on the pulmonary function. Falk-Filipsson A, Löf A, Hagberg M, Hjelm EW, Wang Z J Toxicol Environ Health. Jan. 1993; 38(1):77-88. https://www.ncbi.nlm.nih.gov/pubmed/8421324.
Uptake, distribution and elimination of alpha-pinene in man after exposure by inhalation. Falk AA, Hagberg MT, Löf AE, Wigaeus-Hjelm EM, Wang ZP Scand J Work Environ Health. Oct. 1990; 16(5):372-8. https://www.ncbi.nlm.nih.gov/pubmed/2255878.
Jäger W, Buchbauer G, Jirovetz L, Fritzer M. Percutaneous absorption of lavender oil from a massage oil. J Soc Cosmet Chem. 1992;43:49-54. Jan./Feb. https://pdfs.semanticscholar.org/3530/6465958d8e35e36e7933fa57ba134fe4f9b3.pdf.
Inhalation of vapor from black pepper extract reduces smoking withdrawal symptoms. Rose JE, Behm FM Drug Alcohol Depend. Feb. 1994; 34(3):225-9. https://www.ncbi.nlm.nih.gov/pubmed/8033760.
Rochefort C, Gheusi G, Vincent JD, Lledo PM. Enriched odor exposure increases the number of newborn neurons in the adult olfactory bulb and improves odor memory. J Neurosci. 2002;22:2679-2689. https://www.ncbi.nlm.nih.gov/pubmed/11923433.
Delgado P, Moreno F. Antidepressants and the brain. Int Clin Psychopharmacol. 1999;14(Suppl 1):S9-16. https://www.ncbi.nlm.nih.gov/pubmed/10468323.
Gerdeman GL, Lovinger DM. Emerging roles for endocannabinoids in long-term synaptic plasticity. Br J Pharmacol. 2003;140:781-789. https://www.ncbi.nlm.nih.gov/pmc/articles/PMC1574086/.
PCT International Search Report dated Jun. 24, 2016 for International Application No. PCT/IB2016/050961 (International Filing Date Feb. 25, 2016).
PCT Written Opinion of the International Search Authority dated Jun. 24, 2016 for International Application No. PCT/IB2016/050961 (International Filing Date Feb. 25, 2016).
The extended European search report mailed by European Patent Office dated Oct. 2, 2018 in the corresponding European patent application No. 16754829.6—10 pages.

| Time (min) | Water Temp (°F) | Oil Temp (°F) | Notes: |
|---|---|---|---|
| 0.0 | 66 | 66 | Began with 3750mL (approx. 1gal) of tap water in large stock pot; water level approx. 2/3 of the way up the jar of oil. |
| 0.5 | 66 | 66 | |
| 1.0 | 66 | 66 | |
| 1.5 | 66 | 66 | Oil at high viscosity - entire volume near solid consistency. |
| 2.0 | 67 | 66 | |
| 2.5 | 68 | 66 | |
| 3.0 | 69 | 66 | |
| 3.5 | 70 | 66 | |
| 4.0 | 71 | 66 | |
| 4.5 | 72 | 66 | |
| 5.0 | 74 | 66 | No change in oil viscocity. |
| 5.5 | 75 | 66 | |
| 6.0 | 77 | 66 | |
| 6.5 | 78 | 66 | |
| 7.0 | 80 | 66 | |
| 7.5 | 81 | 66 | |
| 8.0 | 83 | 66 | |
| 8.5 | 84 | 66 | |
| 9.0 | 85 | 66 | |
| 9.5 | 86 | 66 | |
| 10.0 | 87 | 66 | No change in oil viscocity. |
| 10.5 | 88 | 66 | |
| 11.0 | 89 | 66 | |
| 11.5 | 90 | 66 | |
| 12.0 | 90 | 66 | |
| 12.5 | 91 | 66 | |
| 13.0 | 93 | 66 | |
| 13.5 | 93 | 66 | |
| 14.0 | 95 | 66 | |
| 14.5 | 96 | 66 | |
| 15.0 | 97 | 66 | Oil beginning to soften at bottom of jar. |
| 15.5 | 99 | 66 | |
| 16.0 | 101 | 66 | |
| 16.5 | 102 | 66 | |
| 17.0 | 103 | 67 | |
| 17.5 | 104 | 67 | |
| 18.0 | 106 | 67 | |
| 18.5 | 107 | 67 | |
| 19.0 | 108 | 67 | |
| 19.5 | 109 | 67 | |
| 20.0 | 110 | 67 | Slight softening of outer layer of oil; center retains consistency of a solid. |
| 20.5 | 111 | 67 | |
| 21.0 | 112 | 68 | |
| 21.5 | 113 | 68 | |
| 22.0 | 114 | 68 | |
| 22.5 | 114 | 68 | |

FIG. 3A

| Time (min) | Water Temp (°F) | Oil Temp (°F) | Notes: |
|---|---|---|---|
| 23.0 | 115 | 68 | |
| 23.5 | 116 | 68 | |
| 24.0 | 117 | 69 | |
| 24.5 | 118 | 69 | |
| 25.0 | 119 | 69 | Moderate softening of outer layer of oil; center remains solid. |
| 25.5 | 120 | 69 | |
| 26.0 | 121 | 69 | |
| 26.5 | 122 | 69 | |
| 27.0 | 123 | 69 | |
| 27.5 | 124 | 69 | |
| 28.0 | 126 | 69 | |
| 28.5 | 127 | 69 | |
| 29.0 | 128 | 69 | |
| 29.5 | 130 | 69 | |
| 30.0 | 131 | 69 | |
| 30.5 | 132 | 70 | Moderate softening of outer layer; center remains solid. |
| 31.0 | 134 | 70 | |
| 31.5 | 134 | 70 | |
| 32.0 | 135 | 70 | |
| 32.5 | 136 | 70 | |
| 33.0 | 137 | 70 | |
| 33.5 | 138 | 70 | |
| 34.0 | 139 | 70 | |
| 34.5 | 139 | 70 | |
| 35.0 | 140 | 70 | Significant softening of outer layer of oil; center remains solid. |
| 35.5 | 141 | 71 | |
| 36.0 | 142 | 71 | |
| 36.5 | 143 | 71 | |
| 37.0 | 143 | 71 | |
| 37.5 | 144 | 71 | |
| 38.0 | 145 | 72 | |
| 38.5 | 146 | 72 | |
| 39.0 | 146 | 72 | |
| 39.5 | 147 | 72 | Significant softening of outer layer; center slightly softening - "melting" appearance. |
| 40.0 | 148 | 73 | |
| 40.5 | 149 | 73 | Consistency does not lend itself to stirring at this point. |
| 41.0 | 150 | 73 | |
| 41.5 | 151 | 73 | |
| 42.0 | 152 | 74 | |
| 42.5 | 153 | 74 | |
| 43.0 | 154 | 74 | |
| 43.5 | 156 | 75 | |
| 44.0 | 157 | 75 | |
| 44.5 | 158 | 75 | |
| 45.0 | 159 | 75 | Significant softening throughout entire volume of oil; outer layer of oil at liquid viscosity. |
| 45.5 | 160 | 76 | |

FIG. 3B

| Time (min) | Water Temp (°F) | Oil Temp (°F) | Notes: |
|---|---|---|---|
| 46.0 | 162 | 76 | |
| 46.5 | 163 | 76 | Gentle stirring of oil now possible to even out |
| 47.0 | 163 | 77 | heat dispersment; oil nearly at optimum viscosity. |
| 47.5 | 164 | 78 | |
| 48.0 | 164 | 78 | Further stirring. |
| 48.5 | 165 | 79 | |
| 49.0 | 166 | 79 | |
| 49.5 | 166 | 82 | |
| 50.0 | 167 | 84 | Optimum viscosity reached. |
| 50.5 | 167 | 88 | |
| 51.0 | 167 | 90 | |
| 51.5 | 168 | 92 | |
| 52.0 | 169 | 94 | |

FIG. 3C

METHOD FOR CONDUCING CONCENTRATED CANNABIS OIL TO BE STABLE, EMULSIFIABLE AND FLAVORLESS FOR USE IN HOT BEVERAGES AND RESULTING POWDERIZED CANNABIS OIL

CROSS REFERENCE TO RELATED APPLICATIONS

The subject application is a continuation application and claims priority to U.S. Provisional Patent Application Ser. No. 62/120,275, filed on Feb. 24, 2015; U.S. Nonprovisional patent application Ser. No. 15/049,916, filed on Feb. 22, 2016 and issued on Apr. 25, 2017 as U.S. Pat. No. 9,629,886; and U.S. Nonprovisional patent application Ser. No. 15/466,068, filed on Mar. 22, 2017; and all of such applications are incorporated herein in their entirety by this reference thereto.

FIELD OF THE DISCLOSURE

The embodiments of the described invention relate generally to methods and compositions of matter for enabling concentrated cannabis oil to be stable, emulsifiable and flavorless for use in hot beverages or food by combining said oil with a starch powder or starch-derived powder. Embodiments also relate to a variety of culinary uses for the stabilized, emulsified, flavorless concentrated cannabis oil powder.

BACKGROUND

Cannabis, also commonly known as marijuana, is a flowering plant that includes three species or sub-species, namely sativa, indica and ruderalis. The plant is indigenous to Central Asia and the Indian Subcontinent. Cannabis has long been used for hemp fiber, for oils, for medicinal purposes and as a recreational drug. Cannabis plants produce a group of chemicals called cannabinoids. The majority of these compounds are secreted by glandular trichomes that occur abundantly on the floral calyxes and bracts of female cannabis plants. When used by humans medicinally or recreationally, cannabis can be consumed by a variety of routes, including vaporizing or smoking dried flower buds and leaf portions, resins, extracted oils or waxes. However, in recent years many medicinal patients, as well as recreational users, have begun to prefer consuming cannabis in edible form, by eating lozenges, candies, or baked goods, drinking beverages, or by taking capsules.

The most well-known cannabinoid is tetrahydrocannabinol, often abbreviated as "THC." The chemical formula for THC is $C_{21}H_{30}O_2$ and it has the following chemical structure:

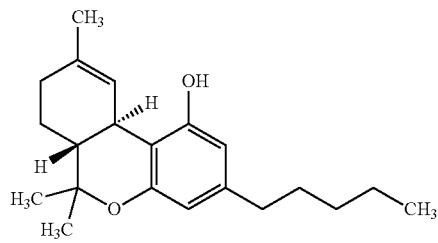 [SMILES: CCCCCc1cc(O)c2c(c1)OC(C)(C)[C@@H]1CCC(C)=C[C@@H]21]

THC is an aromatic terpenoid and is widely recognized as the principal psychoactive constituent in cannabis. THC has a very low solubility in water, but good solubility in most organic solvents, specifically lipids and alcohols.

The cannabis plant produces hundreds of other cannabinoids, terpenoids and other compounds that are only beginning to be identified, studied and categorized. One generally recognized cannabinoid that has medical efficacy is Cannabidiol ("CBD"). It is a major constituent of the plant, second to THC, and represents up to 40% by weight, in its extracts. Compared with THC, CBD is not psychoactive in healthy individuals, and is considered to have a wider scope of medical applications than THC, including for epilepsy, multiple sclerosis spasms, anxiety disorders, bipolar disorder, schizophrenia, nausea, convulsion and inflammation, as well as inhibiting cancer cell growth.

It is also believed by many researchers that many of the other cannabinoids, terpenoids and other compounds may have important health benefits and/or be capable of treating certain human diseases.

There are two characterized cannabinoid receptors in the human body, CB1, which is primarily located in the central nervous system, and CB2 which is primarily located in the immune system and blood cells. These cannabinoid receptors are naturally present and are activated by endocannabinoids that are produced by the human body for neural and cell signaling. In neurons, endocannabinoids bind to the CB1 receptors at the pre-synaptic junction and, among other effects, impact the release of gamma-amino butyric acid ("GABA"). However, when THC is present in the human bloodstream, it binds to these cannabinoid receptors and causes many different psychotropic effects.

Consumption of cannabis by a human generally results in a wide variety of psychotropic effects, but which is often referred to as a "high." The cannabis high varies depending on many factors, including the strain of cannabis, the amount consumed, the method of consumption, the biochemistry of the individual consuming it and the individual's level of experience in consuming cannabis. That said, a cannabis high can include euphoria, anxiety, a general alteration of conscious perception, feelings of well-being, relaxation or stress reduction, increased appreciation of humor, music (especially discerning its various components/instruments) or the arts, joviality, metacognition and introspection, enhanced recollection (episodic memory), increased sensuality, increased awareness of sensation, increased libido, and creativity. Abstract or philosophical thinking, disruption of linear memory and paranoia or anxiety are also typical effects.

Cannabis consumption also often produces many subjective and highly tangible effects, such as greater enjoyment of food taste and aroma, an enhanced enjoyment of music and comedy, and marked distortions in the perception of time and space (where experiencing a "rush" of ideas from the bank of long-term memory can create the subjective impression of long elapsed time, while a clock reveals that only a short time has passed). Many individuals find some of these effects pleasing and enjoyable, while other individuals do not enjoy such effects.

Although cannabis has a high margin of safety, it can produce negative side effects. At higher doses in humans, effects can include altered body image, auditory and/or visual illusions, pseudo-hallucinatory, and ataxia from selective impairment of polysynaptic reflexes. In some cases, in humans, cannabis can lead to dissociative states such as depersonalization and derealization. Additionally, canine studies of very high doses of cannabis resulted in intoxication effects including depression, hypersalivation, mydriasis, hypermetria, vomiting, urinary incontinence, tremors, hypothermia, bradycardia, nystagmus, agitation, tachypnea, ataxia hyperexcitability and seizures. Occasionally, heavy use, or use by inexperienced human consumers, particularly in an unfamiliar environment, can result in very negative experiences. Any episode of acute psychosis that accompanies cannabis use usually abates after 6 hours, but in rare instances heavy users may find the symptoms continuing for many days. If the episode is accompanied by aggression or sedation, physical restraint may be necessary.

While many psychoactive drugs clearly fall into the category of either stimulant, depressant, or hallucinogen, cannabis exhibits a mix of all properties, perhaps leaning the most towards hallucinogenic or psychedelic properties, though with other effects quite pronounced as well. THC is typically considered the primary active component of the cannabis plant.

Cannabis growers have been developing different strains of cannabis plants that have different THC and CBD levels. Recently, medical cannabis users have been demanding medical cannabis products that have CBD as the main active ingredient, and little or no THC, providing some of the medicinal benefits of cannabis without the psychoactive effects caused mainly by THC.

A psychoactive drug, psycho pharmaceutical, or psychotropic is a chemical substance that crosses the blood-brain barrier and acts primarily upon the central nervous system where it affects brain function, resulting in alterations in perception, mood, consciousness, cognition, and behavior. These substances may be used recreationally, to purposefully alter one's consciousness, or as entheogens, for ritual, spiritual, and/or shamanic purposes, as a tool for studying or augmenting the mind. Many psychoactive drugs have therapeutic utility, e.g., as anesthetics, analgesics, or for the treatment of psychiatric disorders.

Psychoactive substances often bring about subjective changes in consciousness and mood that the user may find pleasant (e.g. euphoria) or advantageous (e.g. increased alertness) and are, thus, reinforcing. Thus, many psychoactive substances are abused, that is, used excessively, despite health risks or negative consequences. With sustained use of some substances, psychological and physical dependence ("addiction") may develop, making the cycle of abuse even more difficult to interrupt. Drug rehabilitation aims to break this cycle of dependency, through a combination of psychotherapy, support groups, maintenance and even other psychoactive substances. However, the reverse is also true in some cases, that certain experiences on drugs may be so unfriendly and uncomforting that the user may never want to try the substance again. This is especially true of the deliriants (e.g. Jimson weed) and powerful dissociatives (e.g., Salvia divinorum). Most purely psychedelic drugs are considered to be nonaddictive (e.g. LSD, psilocybin, mescaline). "Psychedelic amphetamines" or empathogenentactogens (such as MDA and MDMA) may produce an additional stimulant and/or euphoriant effect and, thus, have an addiction potential.

In the early twentieth century, it became illegal in most of the world to cultivate or possess cannabis. However, within the last decade, some states and nations have begun to legalize the cultivation, possession and use of cannabis for medical purposes. Currently, the use of medical marijuana is decriminalized or legalized in 32 U.S. states. Cannabis is used to reduce nausea and vomiting during chemotherapy, to improve appetite in people with HIV/AIDS, to treat chronic pain, and help with muscle spasms. Other possible medical uses, which are sometimes disputed, include treatment of multiple sclerosis, AIDS wasting syndrome, epilepsy, rheumatoid arthritis, glaucoma, PTSD, depression and generalized anxiety. However, many patients and consumers are hesitant to try or continue to consume cannabis, particularly in public, due to the negative social stigma and negative health effects of smoking cannabis. Accordingly, there is a need to address the negative social stigma and negative health effects of smoking cannabis, while allowing individuals to still be able to consume it for medical reasons and its health benefits.

Further, within the last two years, several states in the United States have legalized or decriminalized the cultivation, possession and use of Cannabis for recreational purposes. Currently, its use for any purpose by individuals over the age of eighteen has been decriminalized or legalized in four states and the District of Columbia.

As such, some sources estimate that there are many more recreational users of cannabis than ever before, including new or otherwise inexperienced consumers of cannabis. Yet, one significant drawback for new recreational cannabis users, as well as medical patients, is the variability in the amount of THC that is present in any given cannabis product, whether it is a smokable product, an oil, or an edible. Because of this variability, it is often difficult for new cannabis users to correctly gauge the appropriate amount of cannabis to consume, and likewise it is often difficult for medical patients to accurately dose themselves with the proper amount of THC, CBD or other cannabinoids to address their symptoms. As such, there is a need for a product that enables a consumer to use an accurate, standardized dose of THC and CBD.

As discussed above, many medical patients and newer consumers of cannabis now prefer to consume cannabis by eating or drinking it, rather than smoking. Frequently, edibles and drinks containing cannabis are made using extracted cannabis oil. However, to date, cannabis experts and companies manufacturing edibles and drinks containing cannabis have had significant difficulty in producing edibles and drinks that did not have a strong cannabis smell or flavor. Many medical patients and novice users find this smell and taste unpleasant, as, depending on the strains used to create the oil, the smell and taste is reminiscent of a skunk, pine needles, herbs, or is strongly plant-like. This taste and smell is frequently masked by the addition of other strong flavors or sugar, yet this also often proves unsatisfactory. This is particularly true when cannabis oil is added to subtly flavored beverages such as coffee or tea. Accordingly, there is a need in the industry to develop a way to make edibles and beverages containing cannabis oil that do not have a strong cannabis smell or taste.

Moreover, due to the solubility characteristics of cannabis oil, cannabis experts and companies manufacturing oils and drinks containing cannabis have had significant difficulty in producing an oil that can be added to a drink in a way that the oil will be emulsified, or in solution, or evenly distributed throughout the drink. In many cases, the cannabis oil separates in water-based drinks, such as coffee or tea, and is unpleasant to drink. Moreover, such separation can lead to a medical patient not receiving an accurate dose, if the patient does not consume the entire drink, particularly the separated oil portion of the drink.

Accordingly, there is a need for a standardized and measurable dosage of THC and CBD in a powder form, a way to enable consumers of cannabis to accurately and repeatably deliver the same dose of THC and CBD to address their medical needs, a more socially acceptable, easier, and more convenient way to consume cannabis than smoking it, a way to render the normally unpleasant tasting concentrated cannabis oil flavorless, a way to fully capitalize on the medical benefits of CBD in cannabis products, to eliminate or minimize the psychoactive effects of THC, if so desired, in cannabis products, or otherwise control the level of THC in a consumable form, a way for users to control the THC intake and its associated effects without the negative health aspects of inhaling smoke, a way to select cannabis products made from sativa strains, indica strains or combination thereof, and that enables users to achieve the synergistic effect of caffeinated coffees or teas with cannabis, which can create a mildly euphoric effect in certain controlled doses.

SUMMARY OF THE INVENTION

Embodiments of the present invention address the needs described above and relate to making concentrated cannabis oil stable, emulsifiable and flavorless through the addition and mixing of a starch powder, particularly maltodexterin. This concentrated cannabis oil infused powder is effective as a food and beverage additive and could have a high CBD level and a wide range of THC levels, depending on the desired outcome. This concentrated cannabis oil powder can provide users an option to decide the level of acceptable psychoactive effects caused mainly by THC, while getting the medical benefits of CBD.

One object and advantage of the present invention is to provide a standardized and measurable dosage of THC and CBD in a powder form, to enable consumers of cannabis to accurately and repeatably deliver the same dose of THC and CBD to address their medical needs.

Another object and advantage of the present invention is to provide a more socially acceptable, easier, and more convenient way to consume cannabis than smoking it.

Another object and advantage of the present invention is to render the normally unpleasant tasting concentrated cannabis oil flavorless.

Yet another object and advantage of the present invention is to provide a way to fully capitalize on the medical benefits of CBD in cannabis products.

Yet another object and advantage of the present invention is to eliminate or minimize the psychoactive effects of THC, if so desired, in cannabis products, or otherwise control the level of THC in a consumable form.

Yet another object and advantage of the present invention is to provide a way for users to control the THC intake and its associated effects without the negative health aspects of inhaling smoke.

Yet another object and advantage of the present invention is to provide a way to select cannabis products made from sativa strains, indica strains or combination thereof.

Yet another object and advantage of the present invention is to provide a method and compound that enables users to achieve the synergistic effect of caffeinated coffees or teas with cannabis, which can create a mildly euphoric effect in certain controlled doses.

The cannabis oil powder of the present invention is effective for use in applications of hot beverages such as coffees and teas, in single serve beverage brewing cartridges (often referred to as a "K-Cup", which by the registered trademark of Keurig Green Mountain, Inc.) bottled beverages, food/beverage additive packets intended to be poured directly into hot beverages, tea bags, coffee pods/filters, ground coffee and instant coffee forms, as well as in recipes for baked goods or hot foods, where there is a need for different controlled levels of CBD and THC. Additionally, the cannabis oil powder of the present invention lends itself to encapsulation and can be ingested orally in either pill or powder form.

BRIEF DESCRIPTION OF THE DRAWINGS

In the descriptions that follow, like parts or steps are marked throughout the specification and drawings with the same numerals, respectively. The drawing figures are not necessarily drawn to scale and certain figures may be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein:

FIG. 3A is a table showing the temperatures of one pound of cannabis oil and the water of a water bath, varying over time, during the warming step of an embodiment of the process for powderization of cannabis;

FIG. 3B is continuation of the table of FIG. 3A, showing the temperatures of one pound of cannabis oil and the water of a water bath, varying over time, during the warming step of an embodiment of the process for powderization of cannabis;

FIG. 3C is continuation of the table of FIGS. 3A and 3B, showing the temperatures of one pound of cannabis oil and the water of a water bath, varying over time, during the warming step of an embodiment of the process for powderization of cannabis.

DETAILED DESCRIPTION OF THE PREFERRED EMBODIMENTS

The description that follows is presented to enable one skilled in the art to make and use the present invention, and is provided in the context of a particular application and its requirements. Various modifications to the disclosed embodiments will be apparent to those skilled in the art, and the general principles discussed may be applied to other embodiments and applications without departing from the scope and spirit of the invention. Therefore, the invention is not intended to be limited to the embodiments disclosed, but the invention is to be given the largest possible scope which is consistent with the principles and features described herein.

Embodiments of the present invention relate to the process of extracting concentrated cannabis oil from cannabis plant materials and then combining concentrated cannabis oil with a starch powder, such as maltodextrin, to create a concentrated cannabis oil powder. The resulting cannabis oil powder may be used to dose any edible or beverage so that a patient or recreational user can consume an accurately measured dose of THC or CBD. The resulting cannabis oil powder is generally odorless and tasteless when added to edibles and drinks. Moreover, the resulting cannabis oil powder emulsifies quickly and easily in hot beverages, thereby overcoming the historic problem of separation of cannabis oil and water when cannabis oil is added directly to beverages.

Figure 1:
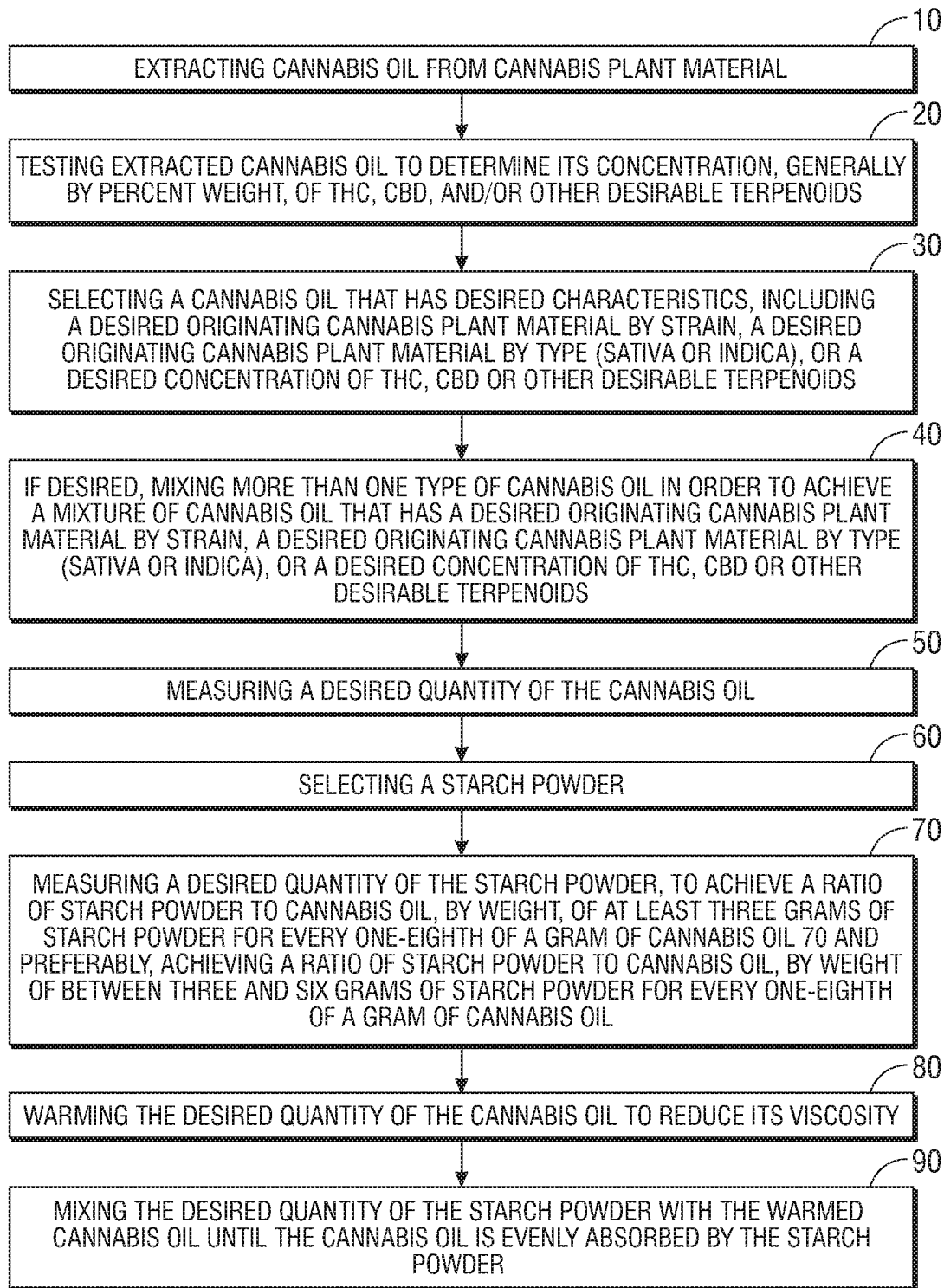
FIG. 1 is a flowchart of an embodiment of the process for powderization of cannabis.
Figure 2:
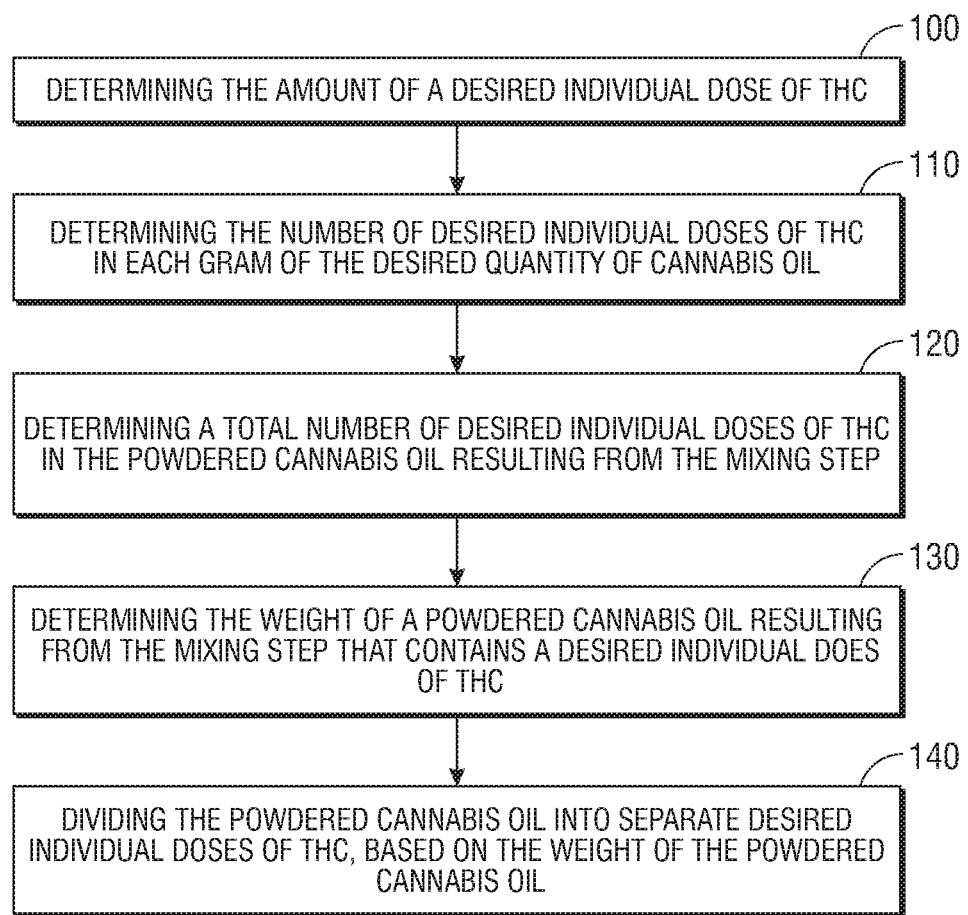
FIG. 2 is a flowchart of further steps in an embodiment of the described powderization process.
Figure 4:
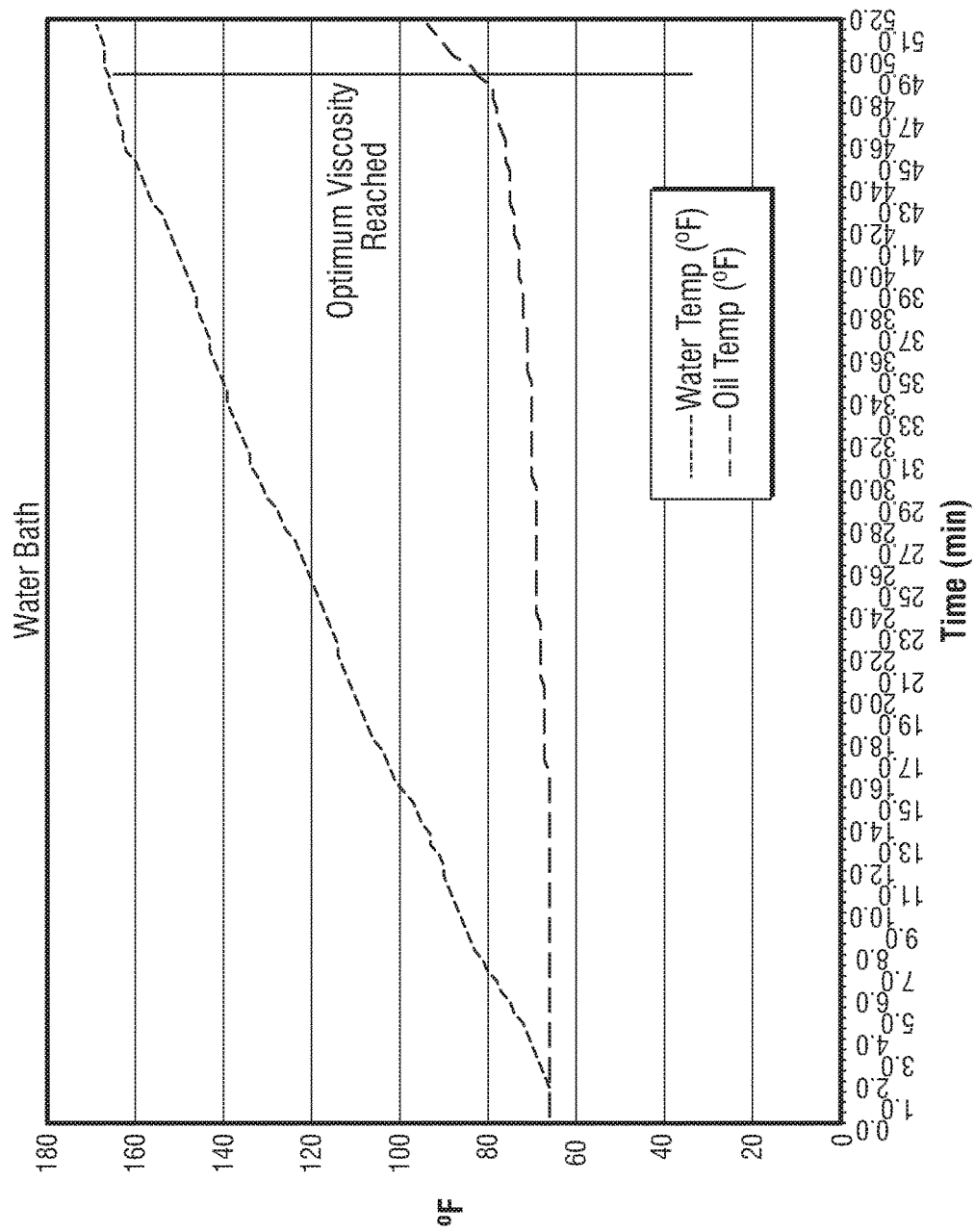
FIG. 4 is a graph showing the relationship of the temperatures of a quantity of cannabis oil and the water of a water bath, varying over time, during the warming step of an embodiment of the process for powderization of cannabis.

Referring to FIG. 1, an embodiment of the process generally includes the following steps:

(a) extracting cannabis oil from cannabis plant material 10;

(b) testing extracted cannabis oil to determine its concentration, generally by percent weight, of THC, CBD, and/or other desirable terpenoids 20;

(c) selecting a cannabis oil that has desired characteristics, including a desired originating cannabis plant material by strain, a desired originating cannabis plant material by type (sativa or indica), or a desired concentration of THC, CBD or other desirable terpenoids 30;

(d) if desired, mixing more than one type of cannabis oil in order to achieve a mixture of cannabis oil that has a desired originating cannabis plant material by strain, a desired originating cannabis plant material by type (sativa or indica), or a desired concentration of THC, CBD or other desirable terpenoids 40;

(e) measuring a desired quantity of the cannabis oil 50;

(f) selecting a starch powder 60;

(g) measuring a desired quantity of the starch powder, to achieve a ratio of starch powder to cannabis oil, by weight, of at least three grams of starch powder for every one-eighth of a gram of cannabis oil 70 and preferably, achieving a ratio of starch powder to cannabis oil, by weight of between three and six grams of starch powder for every one-eighth of a gram of cannabis oil;

(h) warming the desired quantity of the cannabis oil to reduce its viscosity 80;

(i) mixing the desired quantity of the starch powder with the warmed cannabis oil until the cannabis oil is evenly absorbed by the starch powder 90;

Preferably, embodiments of the process also include the following steps shown in FIG. 2:

(j) determining the amount of a desired individual dose of THC 100;

(k) determining the number of desired individual doses of THC in each gram of the desired quantity of cannabis oil 110;

(l) determining a total number of desired individual doses of THC in the powdered cannabis oil resulting from the mixing step 120;

(m) determining the weight of a powdered cannabis oil resulting from the mixing step that contains a desired individual does of THC 130;

(n) dividing the powdered cannabis oil into separate desired individual doses of THC, based on the weight of the powdered cannabis oil 130.

Several variations of the above process exist and are included in the scope of this disclosure. Likewise, although the above steps are a preferred embodiment, not all of the above steps are required to practice the present invention, except as limited by the claims set forth below.

Concentrated Cannabis Oil

Concentrated cannabis oil is made from cannabis plants. Each cannabis strain has a particular cannabinoid (including CBD and THC) profile. Preferably, the concentrated cannabis oil used in the cannabis oil powder of the present invention is extracted from cannabis plants using any number of different extraction processes, discussed below. Depending on the combination of cannabis strains that the concentrated cannabis oil is made from, each batch of concentrated cannabis oil has a different CBD vs. THC ratio, which will be used for different variants of the present invention. Besides the CBD and THC content, concentrated cannabis oil used in the present invention also takes into account the perceived psychoactive effects of the species of cannabis plants used, particularly cannabis sativa and cannabis indica which are both annual herbaceous plants in the cannabis genus. The perceived effects of sativa are well known for its cerebral high, hence it is often used during the daytime as medical cannabis, while indica is perceived as having sedative effects which some prefer for nighttime use. A careful and skillful selection process of cannabis strains is conducted to ensure the concentrated cannabis oil yielded from the extraction, or the concentrated cannabis oil selected from many different batches of extractions, has a particular CBD:THC ratio range and a desirable sativa and indica proportion.

Each batch of concentrated cannabis oil yielded from extraction preferably is sent to a laboratory so that its CBD and THC level can be tested using the liquid chromatography method. Liquid chromatography mass spectrometry (LC-MS, or alternatively HPLC-MS) is an analytical chemistry technique that combines the physical separation capabilities of liquid chromatography (or HPLC) with the mass analysis capabilities of mass spectrometry (MS). Results of the LC-MS test will indicate CBD and THC content by weight in each batch of concentrated cannabis oil. Moreover each batch of concentrated cannabis oil preferably will go through a phenol analysis to determine the phenol level. If desired, various batches of concentrated cannabis oil may be mixed to achieve a mixture that has the desirable CBD:THC ratio and sativa vs. indica proportion. Separation of CBD from THC is also possible during the extraction process, when it is performed using CO2 extraction, and THC and CBD may be blended to attain a desired ratio of CBD to THC.

Modified Starch Maltodextrin 10461 Maltodextrin is a polysaccharide that is used as a food additive. It is produced from starch by partial hydrolysis and is usually found as a white hygroscopic spray-dried powder. Maltodextrin is easily digestible, being absorbed as rapidly as glucose, and might be either moderately sweet or almost flavorless. It is commonly used for the production of sodas and candy. It can also be found as an ingredient in a variety of other processed foods. Maltodextrin consists of D-glucose units connected in chains of variable length. Maltodextrin can be enzymatically derived from any starch. Maltodextrin has no flavor. Maltodextrin has a glycemic index ranging from 85 to 105.

Manufacturing Process

While the manufacturing process for cannabis oil powder may begin with extraction of the concentrated cannabis oil, and a CO2 extracted oil is preferred, commercially available cannabis oil may also be obtained.

To manufacture the cannabis oil powder, first, concentrated cannabis oil with a particular desired THC:CBD ratio and sativa vs. indica or hybrid of the two, proportion is selected. Selections will be based on demand and cyclical availability of plant trimmings related to different harvest seasons. If the desirable THC:CBD ratio concentrated cannabis oil is not available, a few concentrated cannabis oils of different THC:CBD ratios may be mixed to attain the desirable levels.

Extraction

The powderization of cannabis begins with cannabis extract in the form of oil. Essential oils and waxes are extracted from the cannabis plant into their raw, concentrated form. These extracted oils can then be powderized by adding starch-based emulsifiers such as maltodextrin.

Extracted oils are preferable as a base material because of their higher, concentrated THC/CBD content, their properties lend themselves to powderization, and they produce a diminished presence of plant-like tastes and flavors common in edibles infused with other forms of cannabis.

There are numerous ways to extract the essential oils from the cannabis plant. The two most common methods of separating oils and waxes from plant material are mechanical/physical separation and chemical/solvent extraction. Both methodologies have pros and cons regarding time, cost, and potential yields. One thing all methods of extraction have in common is that the resultant yields always depend upon the original condition and quality of the plant material and how it was grown.

Mechanical separation typically involves the use of a screen or filter and cold temperatures. Cold temperatures freeze the tiny trichomes located on plant leaves. Trichomes contain most of the essential oils and waxes intended for extraction. When these trichomes are frozen (typically with ice water or dry ice), they become brittle and break off (separate) from the leaf material. These separated trichomes are then filtered from the leaf material, leaving what is referred to as hash or kief. These materials have a crumbly texture and do not lend themselves to powderization, so this hash product must then be post-processed using a solvent such as ethanol in order to create an oily, fluid consistency. This method, involving the use of ethanol as a solvent, is often referred to as the "Rick Simpson Oil" method, or RSO. Ingesting any solvent, even alcohol, is dangerous so, before consumption, the ethanol must be removed. This can be done by simple evaporation, accelerated by the addition of heat. A rotary evaporator is the best tool for this job due to the ability to keep temperatures relatively low and preserve flavor and terpenes. This process of ice-water extraction is laborious and time consuming and is not a preferred way to obtain concentrates.

Chemical/solvent separation is the preferred method of extraction over mechanical separation because this method returns higher yields, however, the type of solvent is of the utmost importance. Using highly combustible chemical solvents such as butane and propane are rapidly becoming outmoded methods of extraction. They are dangerous during the manufacturing process and if not carefully removed from the resulting oil, they are dangerous to consume. In some cases, these manufacturing methods are becoming outlawed. In addition, post-processing is absolutely critical to ensure the complete removal of the harmful and potentially poisonous solvents.

The safest, cleanest way to extract essential oils from the cannabis plant is to use a CO2 extractor. This type of extraction chamber uses highly pressurized "supercritical" and "subcritical" carbon dioxide gas to pull oils and resins from plant matter. Pressurized CO2 is non-flammable, non-toxic, and though it acts just as a hydrocarbon solvent or organic-chemical solvent would in removing the resinous compounds from cannabis leaf material, CO2 leaves no residual solvent behind. The resulting oils and waxes are solvent-free and generally do not require post-processing. CO2 extractors also keep much of the plant's biochemical properties intact, producing a concentrated oil that contains the same properties as when the oil was growing in bud form. Another unique benefit to using this method is its customization capabilities. Depending on the original biochemical makeup of the plant material, using CO2 extraction chambers allow the manufacturer to create an output with a distinct and specified cannabinoid profile or a specific texture/viscosity depending on how the final product is intended to be used. Fine tuning the machine's temperature and pressure parameters allows the manufacturer to hone the output and achieve a specifically desired product. For example, if a manufacturer intends to make a product with a specific terpene profile for use as a sleep-aid, or if the product is required to have a specific THC:CBD ratio, a CO2 extraction machine can generally accomplish these goals.

The CO2 oil extraction has several advantages over other methods. First, CO2 is non-toxic and is Generally Regarded As Safe (GRAS) by the FDA for use in food products. Other extraction solvents, such as hydrocarbon based propellants like propane and butane, hexane and pentane, or ethanol/alcohol mixtures require additional processing beyond the extraction process in order to ensure the product is safe for consumption. With CO2 oil extraction, no toxins, heavy metals or hydrocarbon materials come in contact with the extracted oils. The spent material is also free of residual contaminates so it can be re-used as well. Second, CO2 is non-flammable. It does not require costly explosion-proof facilities. Third, CO2 is "cold." Using CO2, cannabis oil extractions can be done at temperatures that are native to the plant, minimizing thermal degradation of the plant material and the extracted oil. Fourth CO2 is "tunable." Specifically, the solvency power of CO2 can be adjusted by increasing or decreasing pressures and/or temperatures. Fifth, CO2 is inexpensive and readily available. CO2 oil extraction systems recirculate and subsequently recover 95% of the CO2 used in each extraction. Finally, CO2 is environmentally friendly. It does not contribute to the overall atmospheric CO2 levels.

While the CO2 extraction method is the current preferred method of concentrated cannabis oil extraction, there are multiple methods of producing concentrated cannabis oil. Future technologies may lead to more efficient means of production of concentrated cannabis oil in the future.

After cannabis oil is extracted, a preferred additional step called "winterization" or "de-waxing" should be carried out. Winterization is a post-processing technique used for extracted cannabis oils. While it is not a requirement for the extraction of essential oils, it is sometimes preferred when manufacturing products for vape pens and edibles. Winterization further removes plant waxes, fats, and lipids from the extracted CO2 oil, leaving a thinner, less viscous, and slightly more concentrated product. Ethanol and below-freezing temperatures are used to separate, harden, and remove all remaining waxy materials. The ethanol is then distilled off using the above mentioned rotary evaporator or other distillation technique.

All of the aforementioned methodologies create a cannabis oil product that lends itself to powderization through the addition of starch-based emulsifiers. As the cannabis industry matures and new technologies emerge, new extraction methods will also apply in the powderization of essential cannabis oils and may be useful in the method described herein.

Decarboxylation

There are over 400 chemical compounds that define the chemical makeup of the cannabis plant. THC and CBD are the two most commonly identified compounds, and their symbiotic relationship gives the cannabis plant its many healing attributes. THC content levels are of the utmost importance from the viewpoint of producers of cannabis products. Cultivators, extractors, and edibles manufacturers alike, all regard THC content as the critical aspect that lends (increased) value to their product.

Δ-9-Tetrahydrocannabinol (THC), the main psychoactive component within the chemical makeup of the cannabis plant, is not readily available for consumption and absorption by a user, because in nature the THC exists as carboxylate acid, namely Tetrahydrocannabinolic acid (THCA). THCA is not itself a psychoactive compound, however, studies have shown that it embodies properties such as anti-inflammation, anti-emetic, and neuroprotective aspects. Typically, removal of the carboxyl group is accomplished by a chemical reaction when heat is applied to the THCA, such as when cannabis plant material is smoked. This step is referred to as "decarboxylation" and it must be carried out at some point before or during the consumption of cannabis oil in order for the THC to be available to the consumer.

Edibles producers, unlike cultivators and extractors, face the added task of decarboxylation of their cannabis material before (or after) infusing their products and sending them to market. Otherwise, the edible items, while still containing numerous beneficial cannabinoids, will not induce the intended psychoactive properties. This is because consumers are understandably not expected to smoke or vape an infused brownie or chocolate bar. Instead, the THCA must have already been converted to THC within the infused product, so that ingestion produces the desired effect.

This decarboxylation process can be accomplished in a variety of different ways and at any level of processing. Raw flower, bud or trim can be decarboxylated (without being smoked and before being processed down into concentrates) as can raw concentrates again, without being smoked or vaped and before being infused into edibles. It is up to the edibles manufacturer at which point to decarboxylate their cannabis material, and this decision will be made on the basis of time, cost, availability, feasibility, and convenience.

The most effective tool for decarboxylation of cannabis is a vacuum oven. Conventional ovens will also work, but their temperatures fluctuate significantly, and keeping a steady, precise temperature, not an average temperature, is key to successful decarboxylation. Vacuum ovens also allow for the cannabis to decarboxylate at a relatively low temperature for a longer period of time. Keeping the temperature relatively low also helps prevent boiling off some of the other non-psychoactive yet highly beneficial cannabinoids in the cannabis material. For example, using a conventional oven to decarboxylate cannabis at a temperature of 240 degrees Fahrenheit for 60 minutes will convert most, if not all, of the THCA content into THC. However, in the process, the medicinally beneficial terpenoids and flavonoids with much lower evaporation points will have been boiled off, resulting in the loss of many of the believed and suspected health benefits from these compounds. Rather, using a vacuum oven to decarboxylate cannabis at 120 degrees Fahrenheit for 24 hours will convert THCA into THC and preserve the precious terpene profile.

Powderization

The powderization of cannabis begins with cannabis oil. Essential oils are extracted from the cannabis plant into their pure or raw oil form. These extracted oils can then be powderized by adding starch-based emulsifiers such as maltodextrin. In addition, it is important to note that before beginning any powderization, cannabinoid content, particularly the THC percentage by weight, should be known and verified through lab testing.

Typically, extracted oils from the cannabis plant retain a high viscosity. High-viscosity oils are difficult to manage and their properties contribute to loss and waste in a factory setting. To remedy this, gently warming the oil via water bath transforms the extracted oil into a manageable, low-viscosity liquid. To accomplish this, fill a vessel, such as a pot or laboratory water bath that is large enough to fit the jar or container containing the extracted cannabis oil, with water. Carefully place the jar of oil, preferably uncovered, into the water, making sure not to let any water spill into the oil. Keeping the lid on the jar may cause pressure to build in the container if any bubbles should form. The water level should reach at least halfway up the outside of the oil container.

Place the water bath on low heat to slowly and gently warm the water and therefore, the oil. Slowly and gently heating the oil via water bath ensures an even application of heat and prevents the oil from burning. Preferably, the oil and water are heated over time in accordance with the table and graph shown in FIGS. 3A-C and 4, showing exemplary heating times and temperatures for approximately one pound of cannabis oil being heated in approximately one gallon of water in a water bath. Preferably, the cannabis oil is heated until it is approximately the same viscosity as a light syrup or teriyaki sauce. This preferred oil viscosity is achieved at between 80 and 100 degrees Fahrenheit oil temperature. Even more preferably, the preferred oil viscosity is achieved at between 84 and 90 degrees Fahrenheit oil temperature.

Once the oil has been gently heated and is at a manageable, liquid viscosity, maltodextrin or other suitable human-consumable powder is mixed with the oil using an industrial blender. Commercial equipment, as opposed to hand-blending or a home appliance, is preferred to mix the oil and starch together to ensure total and complete even absorption of the powder by the oil. If the oil and starch are not thoroughly mixed, this will cause "hot spots," i.e., uneven disbursement of the oil in the powderized oil, leading to inaccurate dosing.

To obtain the preferred ratio of maltodextrin to oil, compute the following: at least 3 grams of maltodextrin is preferred for every ⅛ gram of oil to create a powder that will completely emulsify in a hot liquid. First, obtain the weight of the oil in grams. Divide the total weight of the oil into 1/8ths of a gram. To do this, simply divide the weight of the oil by 0.125. Multiply this quotient by 3 to get the total grams of maltodextrin required to powderize the oil. (grams of oil/.125) * 3=grams of maltodextrin to be mixed with oil.

Lower ratios of maltodextrin to oil may also be useful, but are not preferred. For example, a ratio of maltodextrin to cannabis oil of as low as 3 grams of maltodextrin to a half-a-gram of oil will still allow the oil to be powderized in such a way that, when added to hot water, the powder will dissolve and most of the oil will emulsify, with some visible oil droplets at the surface of the hot water. To reiterate, the more powder (emulsifier) that is used, the easier it is for the material to be stable in water and the less oil "residue" will be found on top of the liquid or sides of beverage container, resulting in a more commercially viable product due to its more pleasing appearance, taste and complete mixing.

Once a manufacturer has determined the weight of the maltodextrin required to powderize, slowly add the heated oil to the pre-weighted maltodextrin. Mix thoroughly using an industrial blender until the powder achieves complete uniformity. Visual inspection of the powder should conclude that there are no visible "spots" of oil and the powder is a uniform golden-yellowish color.

From this point, the powder is sent to the lab for testing and dosage corroboration.

Lab tests will aid in honing exact dosage amounts and should always be deferred to when dosing infused products with a specified amount of cannabis. However, to estimate what a single dose will be (use 15 mg THC, for example) the following math can be applied, assuming the original oil was lab tested and THC % is known:

Multiply the THC percentage of the oil by 10. For example, if the THC percentage is known to be 65%, multiply 65 * 10 to get 650. This is the number of milligrams of THC for every one gram of oil.

Since we have determined that a single dose is 15 mg THC, we divide the product from above by 15 to obtain the number of single doses per gram of oil.

650/15=43.3. This means there are 43.3 15 mg doses in a single gram of oil at 65% THC.

(65 * 10=650 mg/g)÷15 mg dose=43.3 doses/g

Next, to obtain the total number of doses in the entire batch of oil, multiply the number of doses per gram of oil (43.3 above) by the total grams of oil originally used. For example, if we originally powderized 1 lb (454 grams) of oil, we would multiply 43.3 * 454 to get 19,658.2 total 15 mg doses in the entire batch of (the now powderized) oil.

43.3 * 454 =19,658.2 total 15 mg doses per batch

After determining the total number of doses per batch, simply divide the total weight of the batch by the total number of doses to obtain the weight of a single dose. According to the example above, if we used 454 grams of oil originally, we would have a total powderized weight of 11,350 grams (25 lbs). Dividing this by the total number of doses will give us an approximation of 0.58 grams of powderized oil for a single dose.

11350÷19658.2=0.5774 grams powderized oil in a single 15 mg dose Due to decimal rounding, these figures, while reasonably accurate, are still approximations and should always be corroborated through lab testing to ensure precise dosage.

Finally, while the above description has been largely directed to the use of maltodextrin, other starch powders, may be used in this process. Additionally, other types of powders fit for human consumption may be used, including but not limited to whey protein isolate, whey protein isolate (both dairy-based and plant-based), xanthan gum/guar gum (guaran), mono- and diglycerides, and carboxymethyl cellulose (cellulose gum) so long as they absorb the oil when blended together, dissolve when added to a liquid, remain dissolved in that liquid and have no post-mixing separation of the powder and the oil.

Uses of the Powderized Cannabis Oil

The resulting stable, emulsifiable and flavorless concentrated cannabis oil infused powder may be added to or used in many different applications where the addition of cannabis is desired. For example, the powderized cannabis oil may be used in a wide variety of recipes, hot beverages, tea bags and single serve beverage brewing cartridges, which are often referred to by the trademark "K-cups," bottled beverages that are brewed hot, food additive packets intended to be poured directly into hot beverages, tea bags, coffee pods/filters, ground coffee and instant coffee packages, as well as added to or used in the manufacture of lozenges, candies and capsules. The amounts of concentrated cannabis oil infused powder added to the aforementioned applications will be produced in varying doses of THC and CBD depending on the desired amount.

To achieve a specific THC/CBD mg dosage in each product, mixing ratios of CO2 extracted cannabis oil and maltodextrin will depend on the potency, determined by lab testing, of the cannabis oil, but are generally preferred to be at least three grams of maltodextrin to each one-eighth of a gram of cannabis oil. In addition, depending on the viscosity of the oil, more or less maltodextrin will be used. Take, for example, a hypothetical batch of CO2 cannabis oil tested at a concentration of 48% THC and 1.7% CBD. This means that every gram of oil at this concentration contains 480 mg of THC and 170 mg of CBD. So, to make one 40 mg product, we mix 0.08 g (40÷480) of oil with approximately 2 grams of maltodextrin to create an infused powder containing 40 mg THC. For an 80 mg product, we mix 0.17 g (80÷480 rounded) of oil with approximately 4 grams of maltodextrin to create the concentrated cannabis oil infused maltodextrin powder containing 80 mg THC.

The infused powder applies to a 40 mg THC dose or an 80 mg THC dose (for example) that can be inserted into a coffee filter/pod directly with the coffee grounds, in a tea bag with the tea leaves, inside a single serve "k-cup" in the filter with the coffee grounds or tea leaves or below the filter at the bottom of the "k-cup," inserted in an instant coffee grounds pack or placed in a packet, like sugar or aspartame, which can be poured directly into a hot beverage or hot soup and or baked into food items. All of the aforementioned applications will have the same efficacy, regardless of how the concentrated cannabis oil infused maltodextrin powder is ingested by a user. Varying amounts of concentrated cannabis oil infused maltodextrin powder can be used to make THC or CBD doses ranging from 5 mg to 200 mg, and up, and preferably between 5 mg and 150 mg, depending on medical need, state restrictions, and consumer demand.

The creation of the concentrated cannabis oil infused maltodextrin powder will take place in a sterile, food grade manufacturing facility. The concentrated cannabis oil infused maltodextrin powder will be precisely added to each of the aforementioned applications through automated, mass production equipment with nitrogen sealed packaging to ensure an 18 month shelf life.

As demonstrated, exact recipes will depend on lab tests and the exact concentrations of each batch of CO2 oil. However, these slight variations in concentration will be compensated for during the manufacturing process. In addition, the product is odorless and tasteless, so there will be no discernible difference from unit to unit from the consumer's perspective. Each k-cup, tea bag, the concentrated cannabis oil infused maltodextrin powder packet or ground coffee will deliver the consistent quality and expected experience to the end user.

Application/Recipes

Additionally, a number of exemplar recipes for making edible products and beverages using cannabis oil powder of the present invention are provided as follows, but are not intended to be limiting.

Gelatin Shots (makes 24×10 mg servings):
Ingredients
1 pkg. (3 oz.) gelatin mix
3 cups hot water
1 cup cold water
240 mg THC powder
24 single-serve paper cups
Directions
Heat 3 cups water to boiling. Stir in gelatin mix and THC powder. Stir for 2 min or until completely dissolved. Add 1 cup cold water. Continue to stir and keep solution well mixed while dispensing equal amounts (approx. ½ oz.) into 24 single-serve paper cups. Refrigerate approximately 4 hours or until gelatin becomes firm, before consuming.

Cookies, most varieties (makes 2-dozen 10 mg cookies):
Ingredients
Any cookie recipe
240 mg THC powder
Directions
Follow recipe as directed. Mix/dissolve THC powder with vegetable oil and/or eggs. If recipe does not call for veg. oil/eggs, THC powder should be added first in the batter-making process. Mix batter VERY thoroughly (with a hand blender) before dispensing 24 equal-sized (about ½ tbsp.) spoonful's onto cookie sheet. Bake as directed.

Brownies, most varieties (makes 12×10 mg brownies):
Ingredients
Any brownie recipe
120 mg THC powder
Directions
Follow recipe as directed. Mix/dissolve THC powder with vegetable oil and/or eggs. If recipe does not call for veg. oil/eggs, THC powder should be added first in the batter-making process. Mix batter VERY thoroughly (with a hand blender) before dispensing into baking tray. Bake as directed. Cut into 12 equal-sized 10 mg squares.

Cupcakes/Muffins, most varieties (makes 12×10 mg cupcakes):
Ingredients
Any cupcake/muffin recipe
120 mg THC powder
Directions
Follow recipe as directed. Mix/dissolve THC powder with vegetable oil and/or eggs. If recipe does not call for veg. oil/eggs, THC powder should be added first in the batter-making process. Mix batter VERY thoroughly (with a hand blender) before dispensing equal amounts of batter into cupcake/muffin tray. Bake as directed.

Pancakes (makes 12×10 mg pancakes):
Ingredients
Any pancake recipe
120 mg THC powder
Directions
Follow recipe as directed. Mix/dissolve THC powder with vegetable oil and/or eggs. If recipe does not call for veg. oil/eggs, THC powder should be added first in the batter-making process. Mix batter VERY thoroughly (with a hand blender) before dispensing equal amounts of batter onto heated skillet.

Cake (makes 12×10 mg cake slices):
Ingredients
Any cake recipe
120 mg THC powder
Directions
Follow recipe as directed. Mix/dissolve THC powder with vegetable oil and/or eggs. If recipe does not call for veg. oil/eggs, THC powder should be added first in the batter-making process. Mix batter VERY thoroughly (with a hand blender) before dispensing batter into baking tray. Bake as directed. Cut into equal-sized 10 mg slices.

Instant Oatmeal (one serving):
Ingredients
1 pkg. (1.5 oz) instant oatmeal
⅔ cup water or milk
10 mg THC powder
Directions
Empty contents of package into a microwave-safe bowl. Add THC powder to dry oats. Add ⅔ cup water or milk and stir. Microwave as directed. Remove from microwave and stir thoroughly before enjoying.

Make-Your-Own K-Cups (single serve coffee brewing cartridge cups):
Ingredients
10 mg THC powder
1 tbsp. coffee or tea
Directions
Before placing the filter, place THC powder at the bottom of the single serve coffee brewing cartridge cup. Place filter. Fill with coffee or tea (approx. 1 tbsp.). Secure lid. Place into any K-cup brewer and operate as instructed. THC powder will permeate certain coffee filters better than others. To avoid any loss of THC powder by filtration, it is recommended to bypass the filter by placing the powder material at the bottom of the cup.

Beverages (e.g., water, lemonade, tea, coffee, hot cocoa, soda, juice, milk, cider, bouillon (broth), shakes and smoothies, etc.):
Ingredients
10 mg THC powder
Consumer's beverage of choice
Directions
Mix/dissolve THC powder into HOT water or HOT beverage
If beverage is not intended to be ingested hot, the liquid may be poured over ice or refrigerated/cooled as desired once the THC powder has already been dissolved. The THC powder will remain emulsified in the beverage after cooling, however, the initial application of the powder must be into a HOT liquid, due to the unique emulsification properties of the powderized oil.
When infusing carbonated beverages that may require the application of a concentrated syrup, it is best to initially heat the syrup and dissolve the THC powder into the heated syrup, then add water and carbonate.
THC powder can be added just as any other ingredient when blending a milkshake or fruit smoothie without the application of any heat. Obviously, the application of heat to a shake or smoothie would deteriorate the quality of such beverages. Adding the THC powder during the blending process lends itself well to making infused shakes/smoothies without heat and does not produce issues like clumping/sticking of oil onto sides of container, if sufficient blending is carried it, i.e. at least 2-3 minutes.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments disclosed.

What is claimed is:

1. A tablet or capsule consisting essentially of cannabis oil and carboxymethyl cellulose, wherein:
the ratio of the carboxymethyl cellulose to the cannabis oil, by weight, is between three grams and six grams of carboxymethyl cellulose to every one-eighth of a gram of cannabis oil.

2. The tablet or capsule of claim 1, wherein the ratio of the carboxymethyl cellulose to the cannabis oil, by weight, is one-eighth of a gram of cannabis oil to every three grams of carboxymethyl cellulose.

3. The tablet or capsule of claim 1, wherein the cannabis oil is evenly absorbed onto and/or within the carboxymethyl cellulose.

4. The tablet or capsule of claim 1, wherein the cannabis oil contains at least 5 milligrams of tetrahydrocannabinol.

5. The tablet or capsule of claim 1, wherein the cannabis oil contains between about 5 milligrams and 200 milligrams of tetrahydrocannabinol.

6. The tablet or capsule of claim 1, wherein the cannabis oil contains 10 milligrams of tetrahydrocannabinol.

7. The tablet or capsule of claim 1, wherein the cannabis oil contains between about 40 milligrams and 80 milligrams of tetrahydrocannabinol.

8. The tablet or capsule pf claim 1, wherein the cannabis oil is a carbon dioxide extracted cannabis oil from cannabis.

9. The tablet or capsule of claim 1, wherein the cannabis oil is an extract from cannabis sativa.

10. The tablet or capsule of claim 1, wherein the cannabis oil is an extract from cannabis indica.

11. The tablet or capsule of claim 1, wherein the cannabis oil is decarboxylated.

12. The tablet or capsule of claim 1, wherein the cannabis oil is from two different strains of cannabis.

13. The tablet or capsule of claim 1, wherein the cannabis oil is a butane extracted cannabis oil from cannabis.

\* \* \* \* \*